United States Patent
Lee et al.

(10) Patent No.: US 10,307,361 B2
(45) Date of Patent: Jun. 4, 2019

(54) VESICLES CONTAINING SACCHARIDE ISOMERATE, HYDROLYZED LUPINE PROTEIN, AND INTERCORNEOCYTE LIPID MIMETICS AS ACTIVE INGREDIENT, AND COMPOSITION FOR SKIN EXTERNAL APPLICATION COMPRISING THE SAME

(71) Applicant: CMS LAB Inc., Seoul (KR)

(72) Inventors: Min-Hye Lee, Hwaseong-si (KR); Young-Chul Ko, Yongin-si (KR); Kang-Min Yoo, Ansan-si (KR); Seung-ki Hong, Daejeon (KR); Jin-Soo Lee, Seoul (KR)

(73) Assignee: CMS LAB INC., Seoul (KR)

( * ) Notice: Subject to any disclaimer, the term of this patent is extended or adjusted under 35 U.S.C. 154(b) by 0 days.

(21) Appl. No.: 15/820,093

(22) Filed: Nov. 21, 2017

(65) Prior Publication Data

US 2018/0140528 A1 May 24, 2018

(30) Foreign Application Priority Data

Nov. 22, 2016 (KR) .......................... 10-2016-0155408

(51) Int. Cl.

| | |
|---|---|
| *A61K 38/00* | (2006.01) |
| *A61K 8/64* | (2006.01) |
| *A61K 8/36* | (2006.01) |
| *A61K 8/55* | (2006.01) |
| *A61K 8/63* | (2006.01) |
| *A61K 8/68* | (2006.01) |
| *A61K 8/73* | (2006.01) |
| *A61Q 19/00* | (2006.01) |
| *A61K 8/14* | (2006.01) |
| *A61K 8/9789* | (2017.01) |
| *A61K 8/34* | (2006.01) |
| *A61K 8/60* | (2006.01) |

(52) U.S. Cl.
CPC ................ *A61K 8/645* (2013.01); *A61K 8/14* (2013.01); *A61K 8/345* (2013.01); *A61K 8/361* (2013.01); *A61K 8/553* (2013.01); *A61K 8/60* (2013.01); *A61K 8/63* (2013.01); *A61K 8/68* (2013.01); *A61K 8/73* (2013.01); *A61K 8/9789* (2017.08); *A61Q 19/00* (2013.01); *A61Q 19/007* (2013.01); *A61K 2800/78* (2013.01)

(58) Field of Classification Search
None
See application file for complete search history.

(56) References Cited

U.S. PATENT DOCUMENTS

| | | | |
|---|---|---|---|
| 2004/0009213 A1 | 1/2004 | Skold | |
| 2011/0195103 A1* | 8/2011 | Perez Arcas | ............ A61K 8/73 424/401 |

* cited by examiner

*Primary Examiner* — Jeanette M Lieb
(74) *Attorney, Agent, or Firm* — Heedong Chae; Lucem, PC

(57) ABSTRACT

The present invention relates to a vesicle containing a saccharide isomerate, a hydrolyzed lupine protein, and an intercorneocyte lipid mimetics as an active ingredient, and a composition for skin external application including the vesicle, and more particularly, to a vesicle including: an aqueous phase part including a saccharide isomerate and a hydrolyzed lupine protein; and an oil phase part including an intercorneocyte lipid mimetics, lysolecithin, and glycerin. The vesicle includes the intercorneocyte lipid mimetics together with the saccharide isomerate and the hydrolyzed lupine protein as contents, so that the vesicle is excellent in a skin barrier recovery function and a skin moisturizing effect upon skin application. In addition, the vesicle is excellent in phase stability, so that the vesicle is suitable to be commercialized as various compositions for skin external application.

6 Claims, 6 Drawing Sheets

VESICLES CONTAINING SACCHARIDE ISOMERATE, HYDROLYZED LUPINE PROTEIN, AND INTERCORNEOCYTE LIPID MIMETICS AS ACTIVE INGREDIENT, AND COMPOSITION FOR SKIN EXTERNAL APPLICATION COMPRISING THE SAME

CROSS-REFERENCE TO RELATED APPLICATION

This application claims the benefit of Korean application No. 10-2016-0155408 filed on Nov. 22, 2016 with the Korean Intellectual Property Office, the disclosure of which is incorporated herein by reference.

BACKGROUND OF THE INVENTION

1. Field of the Invention

The present invention relates to a vesicle containing a saccharide isomerate, a hydrolyzed lupine protein, and an intercorneocyte lipid mimetics as an active ingredient, and a composition for skin external application including the vesicle, and more particularly, to a vesicle including: an aqueous phase part including a saccharide isomerate and a hydrolyzed lupine protein; and an oil phase part including an intercorneocyte lipid mimetics, lysolecithin, and glycerin. The vesicle contains the intercorneocyte lipid mimetics containing an intercorneocyte lipid component together with the saccharide isomerate and the hydrolyzed lupine protein, so that the vesicle is excellent in a skin barrier recovery function and a skin moisturizing effect upon skin application. In addition, the vesicle is excellent in phase stability, so that the vesicle is suitable to be commercialized as various compositions for skin external application.

2. Description of the Related Art

Skin is the most external organ of a body, and is an important organ having various cells and a unique structure, having various functions, and significantly influencing an appearance, an impression or the like. The skin represents a health condition of the body, prevents evaporation of inner body moisture, controls a body temperature, protects a human body from external stimuli such as an ultraviolet ray, and serves as a primary barrier for the human body to prevent invasion of harmful microorganisms and contaminants.

The skin is composed of three layers including epidermis, dermis, and a subcutaneous fat, and the epidermis has stratum corneum to serve as a skin barrier for protecting the human body.

The stratum corneum has an organic complex structure composed of a corneocyte and an intercellular lipid. About 30% of moisture, the intercellular lipid, a natural moisturizing factor (NMF) such as an amino acid, urea, or an organic acid, and sebum are present in healthy stratum corneum to function as the skin barrier. If moisture content of the stratum corneum is reduced, flexibility of the corneocyte is decreased, and a proteinase of a corneodesmosome involved in normal desquamation of keratin may not perform its normal activities, so that keratin at an uppermost portion of the stratum corneum is accumulated and partially desquamated in the form of a lump, and skin barrier dysfunction occurs simultaneously. In addition, dry skin may be caused by the skin barrier dysfunction, and the dry skin may cause secondary skin diseases such as skin aging and bacterial infection.

While a basal cell proliferating in stratum basale of epidermis migrates to the stratum corneum, the basal cell is gradually changed in a form and function thereof to form a keratinocyte. The above process is called keratinization of the keratinocyte. The keratinocyte present in the stratum corneum is desquamated from the skin after a certain period of time, and new keratinocytes migrated from the stratum basale of epidermis perform the function of the desquamated keratinocyte instead. During the keratinization, keratinocytes produce the NMF and the intercellular lipid. In other words, the NMF in the stratum corneum, the intercorneocyte lipid, and the desquamation of the corneocyte are considered to be important factors for skin moisturization.

The NMF in the stratum corneum is important in maintaining the stratum corneum in an appropriately hydrated state. Profilaggrin present in stratum granulosum of epidermis is changed into filaggrin in a final differentiation process of the keratinocyte, and the filaggrin is decomposed into NMFs as it migrates to an upper portion of the stratum corneum. The NMFs generated by decomposing the filaggrin is a powerful moisturizer, which is combined with moisture to maintain the moisture of the stratum corneum and adjusts pH of the stratum corneum to strengthen the stratum corneum. The filaggrin forms a hard and flat structure in the corneocyte when a cornified cell envelope is formed during the final differentiation process of the keratinocyte, thereby serving as a brick of the skin barrier.

When a problem occurs in expression of the filaggrin, a structure of the corneocyte becomes abnormal, and the skin barrier function is deteriorated. Moreover, the NMF of the stratum corneum is decreased, so that the moisture content in the stratum corneum is decreased, and the pH of the stratum corneum is increased. Due to the increase in pH, serine protease, which is a proteolytic enzyme, is activated to destroy the corneodesmosome. Accordingly, the stratum corneum is desquamated at an early stage, resulting in dry skin. In other words, when the expression of filaggrin is promoted in the stratum corneum, an NMF component is increased through hydrolysis of the filaggrin to enhance the skin barrier function, and the density of the corneocyte is increased to implement a robust skin barrier.

The intercellular lipid in the stratum corneum includes 40% to 50% of ceramide, 20% to 25% of cholesterol, 15% to 25% of a free fatty acid, 10% of cholesterol ester, and the like, and fills an intercorneocyte space to give a binding strength between the corneocytes so as to form a lamellar structure with the corneocytes. The stratum corneum having the lamellar structure prevents the NMF and inner body substances from leaking to provide an environment where the epidermis may perform normal biochemical metabolism, and prevents external contaminants from invading the skin. If intercellular lipid componentsor intercellular lipid contents of the stratum corneum become out of balance, the lamellar structure of the corneocyte and the intercellular lipid is not maintained, resulting in loss of NMFs and moisture. Accordingly, the stratum corneum may not maintain an appropriate hydration state, causing dryness of the skin and damaging the skin barrier function.

A dermal epidermal junction (DEJ) composed of a basement membrane is disposed between the epidermis and dermis. The basement membrane of the DEJ is composed of a three-layer structure including lamina lucida, lamina densa, and basal lamina, and includes type IV collagen, type VII collagen, laminin isomer, fibronectin, an antigen of bullous pemphigoid, and the like as components.

Laminin-5, which is a component of the basement membrane, is known to be an origin of an epidermal cell, has an activity of promoting adhesion of the corneocyte, and is important in directly binding the corneocyte with the basement membrane. In other words, defective expression of laminin-5 decreases an adhesive property of the corneocyte, causing skin barrier dysfunction. As another component of the basement membrane, type 4 collagen is a major component of the lamina densa, and is an important factor that affects structural stability of the basement membrane. As described above, laminin-5 and type 4 collagen, which are skin binding proteins, are very important in strengthening the DEJ that connects the epidermis to the dermis and allows the epidermis and dermis to make close contact with each other.

The most important function of the DEJ is to connect the epidermis and the dermis to be joined. The DEJ serves as a support for the epidermal cell with a junction of the epidermis and dermis, controls selective permeation and transport of substances between the epidermis and the dermis, and controls proliferation of the epidermal cell by controlling the differentiation of adjacent skin cells. If the DEJ is damaged, selective permeation and filtration of the substance may not be performed, so that possibility of a contaminant penetrating to the dermis is increased. In addition, a skin structure may not be maintained normally, resulting in overall skin barrier dysfunction.

Researches have been conducted to supply the moisture from the outside or to minimize moisture loss from an inner body in order to maintain appropriate moisture in the skin, and researches have been conducted to improve the skin barrier by using intercellular lipid components. However, since the intercellular lipid components have low solubility and are easy to be crystallized, the intercellular lipid components are not completely dissolved in an oil phase of a typical emulsion-type cosmetic composition, so that the stability of the cosmetic composition is deteriorated. In addition, the intercellular lipid components are difficult to be prepared as an aqueous dispersion composition for skin external application. Further, a composition containing only the intercellular lipid components has not shown a sufficient effect because the composition provides temporary relief of symptoms rather than a fundamental solution of restoring a function of a damaged skin barrier.

Therefore, it is necessary to develop a substance having an excellent effect on the skin moisturization, while fundamentally restoring the damaged barrier.

SUMMARY OF THE INVENTION

The inventors have repeatedly performed the researches to develop a composition for skin external application, capable of improving a skin barrier function and a skin moisturizing effect, and as a result, the present invention is completed.

One object of the present invention is to provide a vesicle containing a saccharide isomerate, a hydrolyzed lupine protein, and an intercorneocyte lipid mimetics as an active ingredient, and a composition for skin external application including the vesicle.

To achieve the objects described above, according to the present invention, there is provided the vesicle containing the saccharide isomerate, the hydrolyzed lupine protein, and the intercorneocyte lipid mimetics as the active ingredient, and the composition for the skin external application including the vesicle.

In the vesicle containing the saccharide isomerate, the hydrolyzed lupine protein, and the intercorneocyte lipid mimetics as the active ingredient according to the present invention, the intercorneocyte lipid mimetics containing a intercorneocyte lipid component by a ratio similar to that of an intercellular lipid of a human body is contained together with the saccharide isomerate and the hydrolyzed lupine protein to express filaggrin, laminin-5, and type 4 collagen, thereby improving the skin barrier function and reducing transepidermal water loss (TEWL).

In addition, the vesicle containing the saccharide isomerate, the hydrolyzed lupine protein, and the intercorneocyte lipid mimetics as the active ingredient according to the present invention is excellent in the phase stability, so that the vesicle can be prepared as an aqueous dispersion composition for skin external application, and can be suitable to be commercialized as various compositions for skin external application.

DETAILED DESCRIPTION OF THE INVENTION

Figure 1:
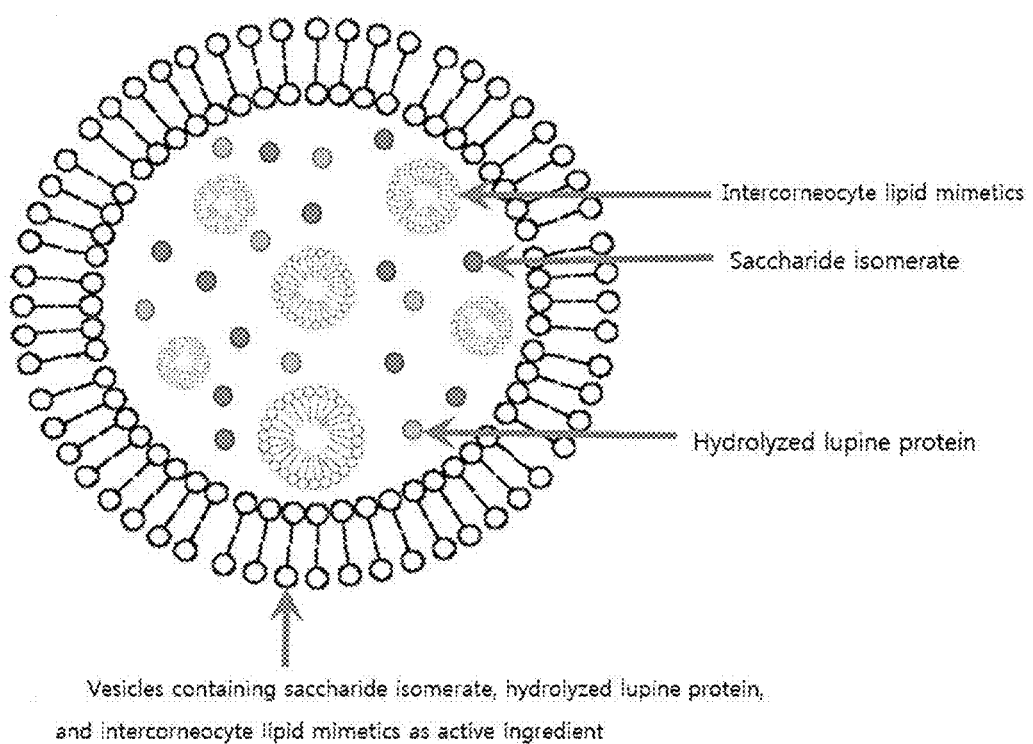
FIG. 1 is a schematic view showing a vesicle containing a saccharide isomerate, a hydrolyzed lupine protein, and an intercorneocyte lipid mimetics as an active ingredient according to one embodiment of the present invention.

Hereinafter, the present invention will be described in detail.

The present invention provides a vesicle containing a saccharide isomerate, a hydrolyzed lupine protein, and an intercorneocyte lipid mimetics as an active ingredient, and a composition for skin external application including the vesicle.

According to the present invention, the vesicle containing the saccharide isomerate, the hydrolyzed lupine protein, and the intercorneocyte lipid mimetics includes: an oil phase part obtained by dispersing 10 wt % to 75 wt % of the intercorneocyte lipid mimetics and 1 wt % to 15 wt % of lysolecithin in 1 wt % to 25 wt % of glycerin; and an aqueous phase part obtained by dissolving 0.01 wt % to 7 wt % of the saccharide isomerate and 0.01 wt % to 7 wt % of the hydrolyzed lupine protein in the balance of purified water based on a total weight of the vesicle.

The content of the intercorneocyte lipid mimetics is preferably 10 wt % to 75 wt % based on the total weight of the vesicle. If the content of the intercorneocyte lipid mimetics is less than 10 wt %, a skin moisturizing effect and a skin barrier recovery effect become insignificant. If the content of the intercorneocyte lipid mimetics is greater than 75 wt %, the content of other components is relatively reduced, so that the vesicle may not be formed in a spherical shape, and an effect of promoting expression of filaggrin, laminin-5 and type 4 collagen is decreased.

The lysolecithin stabilizes the intercorneocyte lipid mimetics, and forms a membrane of the vesicle containing the saccharide isomerate, the hydrolyzed lupine protein, and the intercorneocyte lipid mimetics. The content of lysolecithin is preferably 1 wt % to 15 wt % based on the total weight of the vesicle. If the content of the lysolecithin is less than 1 wt %, a particle size of the vesicle becomes large, so that the intercorneocyte lipid mimetics may not be stabilized, and the stability of the vesicle may be decreased. If the content of the lysolecithin is greater than 15 wt %, the particle size of the vesicle becomes small, so that the rate of the saccharide isomerate, the hydrolyzed lupine protein, and the intercorneocyte lipid mimetics contained in the vesicle may be decreased, and skin irritation may be caused by lysolecithin.

The content of the glycerin is preferably 1 wt % to 25 wt % based on the total weight of the vesicle. If the content of the glycerin is less than 1 wt %, the lysolecithin is not sufficiently dispersed, so that the vesicle may not be formed in a spherical shape. If the content of the glycerin is greater than 25 wt %, it is difficult to arrange a lipid component, and it may be sticky and may give a stifling feeling upon skin application.

The saccharide isomerate exhibits effects of increasing the moisture content of the skin and enhancing the skin barrier by increasing the expression of filaggrin, which is a factor for enhancing the skin barrier. The content of the saccharide isomerate is preferably 0.01 wt % to 7 wt % based on the total weight of the vesicle. If the content of the saccharide isomerate is less than 0.01 wt %, the effect of expressing filaggrin may be insignificant. If the content of the saccharide isomerate is greater than 7 wt %, a degree of increase in the expression of filaggrin based on increase inthe content of the saccharide isomerate may be insignificant.

The hydrolyzed lupine protein exhibits effects of promoting differentiation of keratinocytes and strengthening the skin barrier by increasing the expression of laminin-5 and type 4 collagen. The content of the hydrolyzed lupine protein is preferably 0.01 wt % to 7 wt % based on the total weight of the vesicle. If the content of the hydrolyzed lupine protein is less than 0.01 wt %, the effect of expressing laminin-5 and type 4 collagen may be insignificant. If the content of the hydrolyzed lupine protein is greater than 7 wt %, a degree of increase in the expression of laminin-5 and type 4 collagen based on increase in the content of hydrolyzed lupine protein may be insignificant.

The intercorneocyte lipid mimetics may include 10 wt % to 70 wt % of an intercorneocyte lipid component, 0.1 wt % to 20 wt % of an amphoteric surfactant, 2 wt % to 20 wt % of saturated lecithin, 5 wt % to 20 wt % of glycerin, and the balance of purified water based on a total weight of the intercorneocyte lipid mimetics.

The content of the intercorneocyte lipid component is preferably 10 wt % to 70 wt % based on the total weight of the intercorneocyte lipid mimetics. If the content of the intercorneocyte lipid component is less than 10 wt %, the skin moisturizing effect of the vesicle may become insignificant. If the content of the intercorneocyte lipid component is greater than 70 wt %, the stability of the intercorneocyte lipid mimetics may be decreased due to hydrophobicity and a property of being easily crystallized of the intercorneocyte lipid component.

The intercorneocyte lipid component may include 5 wt % to 60 wt % of ceramide, 5 wt % to 35 wt % of a cholesterol derivative containing cholesterol or a phytosterol derivative containing phytosterol, and 5 wt % to 60 wt % of a higher fatty acid based on a total weight of the intercorneocyte lipid component.

The cholesterol derivative containing cholesterol is preferably a mixture of cholesterol and cholesterol derivatives. The cholesterol derivative preferably includes at least one selected from the group consisting of cholesteryl macadamiate and cholesteryl lanolate.

The phytosterol derivative containing phytosterol is preferably a mixture of phytosterol and phytosterol derivatives. The phytosterol derivative preferably includes at least one selected from the group consisting of phytosterol macadamia nut fatty acid ester, phytosteryl ricebranate, phytosteryl macadamiate, phytosteryl oleate, phytosteryl isostearate, phytosteryl canola glyceride, and phytosteryl hydroxystearate.

The higher fatty acid is preferably a mixture of a palmitic acid, a stearic acid, an oleic acid, and a linolenic acid, and is preferably obtained by mixing palmitic acid: stearic acid:oleic acid:linolenic acid in a weight ratio of 1 to 5:1 to 10:1 to 6:1 to 4. The amphoteric surfactant simultaneously contains cation charges and anion charges, and preferably includes at least one selected from the group consisting of glyceryl lanolate, glyceryl linolenate, glyceryl linoleate, glyceryl ricinoleate, glyceryl myristate, glyceryl behenate, glyceryl stearate, glyceryl stearate citrate, glyceryl olivate, glyceryl oleate, glyceryl undecylenate, glyceryl isostearate, glyceryl cocoate, and glyceryl palmitate. The content of the amphoteric surfactant is preferably 0.1 wt % to 20 wt % based on the total weight of the intercorneocyte lipid mimetics. If the content of the amphoteric surfactant is less than 0.1 wt %, the intercorneocyte lipid component may not be stabilized, so that formation of the intercorneocyte lipid mimetics may be inhibited, possibility of precipitation may be increased, and formation of the vesicle containing the intercorneocyte lipid mimetics is also inhibited, thereby decreasing the stability of the vesicle. In addition, if the content of the amphoteric surfactant is greater than 20 wt %, skin irritation may be caused by the amphoteric surfactant.

The saturated lecithin forms a membrane of the intercorneocyte lipid mimetics containing the intercorneocyte lipid component, and the content of the saturated lecithin is preferably 2 wt % to 20 wt % based on the total weight of the intercorneocyte lipid mimetics. If the content of the saturated lecithin is less than 2 wt %, the intercorneocyte lipid mimetics may not be formed in a spherical shape or the particle size of the intercorneocyte lipid mimetics may increase, so that the stability of the vesicle containing the intercorneocyte lipid mimetics may be decreased. If the content of the saturated lecithin is greater than 20 wt %, the particle size of the intercorneocyte lipid mimetics decreases, resulting in decrease in the content of the intercorneocyte lipid component contained in the intercorneocyte lipid mimetics, so that an effect of enhancing the skin barrier and a moisturizing effect may become insignificant, and skin irritation may be caused by the saturated lecithin.

The content of the glycerin is preferably 5 wt % to 20 wt % based on the total weight of the intercorneocyte lipid mimetics. If the content of the glycerin is less than 5 wt %, the saturated lecithin and the intercorneocyte lipid component may not be sufficiently dispersed, so that the intercorneocyte lipid mimetics may not be easily formed. If the content of the glycerin is greater than 20 wt %, the content of other components is relatively reduced, so that effects of other components may not be ensured.

Referring to FIG. 1, according to the present invention, the vesicle is configured to contain the saccharide isomerate, the hydrolyzed lupine protein, and the intercorneocyte lipid mimetics while being collected by the lysolecithin.

According to the present invention, the vesicle contains and stabilizes the saccharide isomerate, the hydrolyzed lupine protein, and the intercorneocyte lipid mimetics through the above structure, so that the saccharide isomerate, the hydrolyzed lupine protein, and the intercorneocyte lipid mimetics may be effectively absorbed into the skin to express filaggrin, laminin-5 and type-4 collagen, and the vesicle may be excellent in enhancing the skin barrier function and the skin moisturizing effect. In addition, since the vesicle contains the saccharide isomerate, the hydrolyzed lupine protein, and the intercorneocyte lipid mimetics together, the effect of improving the skin barrier is enhanced.

In addition, according to the present invention, the vesicle stabilizes the intercorneocyte lipid component by forming a double membrane with the saturated lecithin, the amphoteric surfactant, and the lysolecithin, so that the vesicle may be excellent in the phase stability, may be prepared as an aqueous dispersion composition for skin external application, and may be suitable to be commercialized as various compositions for skin external application.

Preferably, according to the present invention, the vesicle containing the saccharide isomerate, the hydrolyzed lupine protein and the intercorneocyte lipid mimetics as the active ingredient may be applied to various fields, and more specifically, the vesicle may be included in the composition for the skin external application.

The composition for the skin external application may be manufactured in various types of formulations, and may be appropriately selected according to the purpose. For example, the composition for the skin external application may be prepared as at least one formulation selected from the group consisting of a liquid phase, a suspension phase, an emulsion phase, a gel phase, a cream phase, an ointment phase, a spray phase, and a paste phase, but is not limited thereto. In more detail, the composition for the skin external application may be manufactured in the form of an emollient, a nutritional skin toner, a nourishing cream, a massage cream, an essence, an eye cream, a cleansing cream, a cleansing foam, a cleansing water, a mask pack, a spray, a powder, or a lipstick.

In addition, the composition for the skin external application may contain other components blended in a typical cosmetic composition as necessary. For example, the composition for the skin external application may include a moisturizing agent, an organic or inorganic pigment, an ultraviolet absorber, an antioxidant, a pH adjusting agent, an alcohol, a coloring agent, a perfuming agent, and the like.

Hereinafter, the present invention will be described in more detail with reference to examples. Although the examples are given for describing the present invention in more detail, the scope of the present invention is not limited by the examples.

<Examples 1 to 14> Preparation of Intercorneocyte Lipid Mimetics

An intercorneocyte lipid mimetics is prepared by the following preparation method to have components and compositions shown in Table 1 below.

Step 1: The saturated lecithin, the surfactant and the intercorneocyte lipid components shown in Table 1 below are introduced to the glycerin shown in Table 1 below, and dispersed in the glycerin with an agitator at 80 r to prepare a dispersion solution.

Step 2: The dispersion solution of Step 1 is introduced to the purified water shown in Table 1 below, and agitated with a high-pressure homogenizer at 17,000 rpm for 20 minutes to prepare the intercorneocyte lipid mimetics.

TABLE 1

| | Component | Content (wt %) | | | | | | |
|---|---|---|---|---|---|---|---|---|
| | | Example 1 | Example 2 | Example 3 | Example 4 | Example 5 | Example 6 | Example 7 |
| Intercorneocyte lipid component | Ceramide | 20 | 20 | 20 | 20 | 20 | 20 | 20 |
| | Phytosterol | 12 | 12 | 12 | 12 | 12 | 12 | 12 |
| | Phytosterol macadamia nut fatty acid ester | 4 | 4 | 4 | 4 | 4 | 4 | 4 |
| | Palmitic acid | 1.5 | 1.5 | 1.5 | 1.5 | 1.5 | 1.5 | 1.5 |
| | Stearic acid | 2.5 | 2.5 | 2.5 | 2.5 | 2.5 | 2.5 | 2.5 |
| | Oleic acid | 0.4 | 0.4 | 0.4 | 0.4 | 0.4 | 0.4 | 0.4 |
| | Linolenic acid | 0.6 | 0.6 | 0.6 | 0.6 | 0.6 | 0.6 | 0.6 |
| Surfactant | Glyceryl stearate | 0.05 | 0.1 | 5 | 10 | 20 | 25 | 10 |
| | Saturated lecithin | 4 | 4 | 4 | 4 | 4 | 4 | 1 |
| | Glycerin | 10 | 10 | 10 | 10 | 10 | 10 | 10 |
| | Purified water | 44.95 | 44.90 | 40 | 35 | 25 | 20 | 38 |

| | | Content (wt %) | | | | | | |
|---|---|---|---|---|---|---|---|---|
| | | Example 8 | Example 9 | Example 10 | Example 11 | Example 12 | Example 13 | Example 14 |
| Intercorneocyte lipid component | Ceramide | 20 | 20 | 20 | 20 | 34 | 35 | 40 |
| | Phytosterol | 12 | 12 | 12 | 12 | 15 | 21 | 20 |
| | Phytosterol macadamia nut fatty acid ester | 4 | 4 | 4 | 4 | 4 | 7 | 7 |
| | Palmitic acid | 1.5 | 1.5 | 1.5 | 1.5 | 1.5 | 2 | 2 |
| | Stearic acid | 2.5 | 2.5 | 2.5 | 2.5 | 2.5 | 4 | 4 |
| | Oleic acid | 0.4 | 0.4 | 0.4 | 0.4 | 0.4 | 0.4 | 0.4 |
| | Linolenic acid | 0.6 | 0.6 | 0.6 | 0.6 | 0.6 | 0.6 | 0.6 |
| Surfactant | Glyceryl stearate | 10 | 10 | 10 | 10 | 10 | 10 | 10 |
| | Saturated lecithin | 2 | 10 | 20 | 25 | 4 | 4 | 4 |
| | Glycerin | 10 | 10 | 10 | 10 | 10 | 10 | 10 |
| | Purified water | 37 | 29 | 19 | 14 | 18 | 6 | 2 |

<Examples 15 to 28> Production of Vesicle

The intercorneocyte lipid mimetics prepared in Examples 1 to 14 is mixed with lysolecithin, the glycerin, a saccharide isomerate, a hydrolyzed lupine protein, and purified water by the following production method to produce a vesicle.

Step 1: An oil phase part is prepared by introducing and dispersing 3 wt % of lysolecithin in 3 wt % of glycerin, adding 50 wt % of the intercorneocyte lipid mimetics of Examples 1 to 14 thereto according to Table 2 below, and dispersing with the agitator at 80° C.

Step 2: An aqueous phase part is prepared by dissolving 4 wt % of the saccharide isomerate and 2 wt % of the hydrolyzed lupine protein in 38 wt % of the purified water at 50° C., and production of the vesicle is completed by introducing the oil phase part of Step 1 to the aqueous phase part, agitating with the high-pressure homogenizer at 17,000 rpm for 20 minutes, and treating with ultrasonic waves at 100 W for 20 minutes for homogenization.

TABLE 2

Intercorneocyte lipid mimetics used in examples 15 to 28

| | |
|---|---|
| Example 15 | 50 wt % of the intercorneocyte lipid mimetics of example 1 |
| Example 16 | 50 wt % of the intercorneocyte lipid mimetics of example 2 |
| Example 17 | 50 wt % of the intercorneocyte lipid mimetics of example 3 |
| Example 18 | 50 wt % of the intercorneocyte lipid mimetics of example 4 |
| Example 19 | 50 wt % of the intercorneocyte lipid mimetics of example 5 |
| Example 20 | 50 wt % of the intercorneocyte lipid mimetics of example 6 |
| Example 21 | 50 wt % of the intercorneocyte lipid mimetics of example 7 |
| Example 22 | 50 wt % of the intercorneocyte lipid mimetics of example 8 |
| Example 23 | 50 wt % of the intercorneocyte lipid mimetics of example 9 |
| Example 24 | 50 wt % of the intercorneocyte lipid mimetics of example 10 |
| Example 25 | 50 wt % of the intercorneocyte lipid mimetics of example 11 |
| Example 26 | 50 wt % of the intercorneocyte lipid mimetics of example 12 |
| Example 27 | 50 wt % of the intercorneocyte lipid mimetics of example 13 |
| Example 28 | 50 wt % of the intercorneocyte lipid mimetics of example 14 |

<Examples 29 to 34> Production of Vesicle

As shown in Test example 1 below, the vesicle of Example 26 containing 50 wt % of the intercorneocyte lipid mimetics of Example 12 was excellent in water dispersion stability. Therefore, the intercorneocyte lipid mimetics prepared in Example 12 was mixed with other components by the following production method according to the composition shown in Table 3 below to produce a vesicle.

Step 1: An oil phase part is prepared by introducing and dispersing the lysolecithin in the glycerin, adding the intercorneocyte lipid mimetics of Example 12 thereto according to Table 3 below, and dispersing with the agitator at 80° C.

Step 2: An aqueous phase part is prepared by dissolving the saccharide isomerate and the hydrolyzed lupine protein in the purified water at 50° C., and production of the vesicle is completed by introducing the oil phase part of Step 1 to the aqueous phase part, agitating with the high-pressure homogenizer at 17,000 rpm for 20 minutes, and treating with ultrasonic waves at 100 W for 20 minutes for homogenization.

TABLE 3

| | Content (wt %) | Example 29 | Example 30 | Example 31 | Example 32 | Example 33 | Example 34 |
|---|---|---|---|---|---|---|---|
| Oil phase part | Intercorneocyte lipid mimetics of example 12 | 10 | 10 | 10 | 10 | 10 | 10 |
| | Lysolecithin | 0.5 | 1 | 5 | 10 | 15 | 20 |
| | Glycerin | 3 | 3 | 3 | 3 | 3 | 3 |
| Aqueous phase part | Saccharide isomerate | 4 | 4 | 4 | 4 | 4 | 4 |
| | Hydrolyzed lupine protein | 2 | 2 | 2 | 2 | 2 | 2 |
| | Purified water | 80.5 | 80 | 76 | 71 | 66 | 61 |

<Examples 35 to 40> Production of Vesicle

The intercorneocyte lipid mimetics prepared in Example 12 was mixed with other components by the production method of Examples 29 to 34 according to the composition shown in Table 4 below to produce a vesicle.

TABLE 4

| | Content (wt %) | Example 35 | Example 36 | Example 37 | Example 38 | Example 39 | Example 40 |
|---|---|---|---|---|---|---|---|
| Oil phase part | Intercorneocyte lipid mimetics of example 12 | 5 | 10 | 30 | 50 | 75 | 80 |
| | Lysolecithin | 3 | 3 | 3 | 3 | 3 | 3 |
| | Glycerin | 3 | 3 | 3 | 3 | 3 | 3 |

TABLE 4-continued

|  | Content (wt %) | Example 35 | Example 36 | Example 37 | Example 38 | Example 39 | Example 40 |
|---|---|---|---|---|---|---|---|
| Aqueous phase part | Saccharide isomerate | 4 | 4 | 4 | 4 | 4 | 4 |
|  | Hydrolyzed lupine protein | 2 | 2 | 2 | 2 | 2 | 2 |
|  | Purified water | 80.5 | 80 | 76 | 71 | 66 | 61 |

<Examples 41 to 46> Production of Vesicle

A vesicle is produced by the production method of Examples 29 to 34 to have components and compositions shown in Table 5 below.

TABLE 5

|  | Content (wt %) | Example 41 | Example 42 | Example 43 | Example 44 | Example 45 | Example 46 |
|---|---|---|---|---|---|---|---|
| Oil phase part | Intercorneocyte lipid mimetics of example 12 | 10 | 10 | 10 | 10 | 10 | 10 |
|  | Lysolecithin | 3 | 3 | 3 | 3 | 3 | 3 |
|  | Glycerin | 3 | 3 | 3 | 3 | 3 | 3 |
| Aqueous phase part | Saccharide isomerate | 0.005 | 0.01 | 1 | 5 | 7 | 9 |
|  | Hydrolyzed lupine protein | 0.005 | 0.01 | 1 | 5 | 7 | 9 |
|  | Purified water | 83.99 | 83.98 | 82 | 74 | 70 | 66 |

<Comparative Examples 1 to 3> Preparation of Single Membrane Vesicle

A single membrane vesicle is prepared by the following preparation method to have components and compositions shown in Table 6 below.

Step 1): First, an oil phase part is prepared by introducing ceramide, phytosterol, phytosterol macadamia nut fatty acid ester, a palmitic acid, a stearic acid, an oleic acid, a linoleic acid, caprlic/capric triglyceride and saturated lecithin to glycerin, dispersing with the agitator at 80° C.

Step 2): An aqueous phase part is prepared by dissolving the saccharide isomerate and the hydrolyzed lupine protein in the purified water at 50° C., and production of the single membrane vesicle is completed by introducing the oil phase part of Step 1) to the aqueous phase part, agitating with a homomixer at 3,000 rpm for 5 minutes, and passing through a high-pressure emulsifier three times at a pressure of 600 bar for homogenization.

TABLE 6

|  |  | Content (wt %) | | |
|---|---|---|---|---|
| Component | | Comparative example 1 | Comparative example 2 | Comparative example 3 |
| Oil phase part | Ceramide | 0.1 | 10 | 17 |
|  | Phytosterol | 0.01 | 1 | 7.5 |
|  | Phytosterol macadamia nut fatty acid ester | — | — | 2 |
|  | Palmitic acid | — | — | 0.75 |
|  | Stearic acid | — | — | 1.25 |
|  | Oleic acid | — | — | 0.2 |
|  | Linolenic acid | — | — | 0.3 |
|  | Caprlic/capric triglyceride | 5 | 5 | 5 |
|  | Saturated lecithin | 4 | 4 | 4 |
|  | Glycerin | 10 | 10 | 10 |
| Aqueous phase part | Saccharide isomerate | 4 | 4 | 4 |
|  | Hydrolyzed lupine protein | 2 | 2 | 2 |
|  | Purified water | 74.89 | 64 | 17 |

<Test Example 1> Evaluation of Water Dispersion Stability

In order to examine water dispersion stability of the vesicles of Examples 15 to 34 and the single membrane vesicles of Comparative examples 1 to 3 prepared as above, an identical amount of purified water was added to each of the vesicles of Examples 15 to 34 and the single membrane vesicles of Comparative examples 1 to 3, and dispersed with the agitator at room temperature for 10 minutes. Thereafter, the resultant samples were stored in a thermostatic chamber controlled at a relative humidity of 70±5% and a temperature of 25° C., and precipitation and isolation phenomena were observed over time immediately after mixing. The observation results are shown in Table 7 below.

TABLE 7

|  | Immediately after mixing | After one hour | After 24 hours | After seven days | After 14 days |
|---|---|---|---|---|---|
| Example 15 | ○ | Δ | X | X | X |
| Example 16 | ⊚ | ○ | ○ | ○ | ○ |
| Example 17 | ⊚ | ⊚ | ⊚ | ⊚ | ⊚ |

TABLE 7-continued

|  | Immediately after mixing | After one hour | After 24 hours | After seven days | After 14 days |
|---|---|---|---|---|---|
| Example 18 | ◎ | ◎ | ◎ | ◎ | ◎ |
| Example 19 | ◎ | ◎ | ◎ | ◎ | ◎ |
| Example 20 | ◎ | ◎ | ◎ | ◎ | ◎ |
| Example 21 | ◎ | ○ | ○ | Δ | X |
| Example 22 | ◎ | ◎ | ◎ | ○ | ○ |
| Example 23 | ◎ | ◎ | ◎ | ◎ | ◎ |
| Example 24 | ◎ | ◎ | ◎ | ◎ | ◎ |
| Example 25 | ◎ | ◎ | ◎ | ◎ | ◎ |
| Example 26 | ◎ | ◎ | ◎ | ◎ | ◎ |
| Example 27 | ◎ | ◎ | ◎ | ○ | ○ |
| Example 28 | ◎ | ◎ | ○ | Δ | X |
| Example 29 | ○ | ○ | Δ | X | X |
| Example 30 | ◎ | ◎ | ◎ | ◎ | ○ |
| Example 31 | ◎ | ◎ | ◎ | ◎ | ◎ |
| Example 32 | ◎ | ◎ | ◎ | ◎ | ◎ |
| Example 33 | ◎ | ◎ | ◎ | ◎ | ◎ |
| Example 34 | ◎ | ◎ | ◎ | ◎ | ◎ |
| Comparative example 1 | ○ | Δ | Δ | X | X |
| Comparative example 2 | Δ | Δ | X | X | X |
| Comparative example 3 | Δ | X | X | X | X |

◎: Very stable,
○: Stable,
Δ: Unstable (Slightlyisolated),
X: Completelyisolated (Precipitation)

Examples 15 to 20 were made with different contents of the surfactant, and it is found by comparing Examples 15 to 20 with each other that Example 15 has a phase completely isolated after 24 hours, and Examples 16 to 20 have phases that remain stable even after 14 days. In other words, if the content of the surfactant contained in the intercorneocyte lipid mimetics is less than or equal to 0.05 wt %, the intercorneocyte lipid component may not be stabilized, so that the intercorneocyte lipid mimetics may not be stabilized, and the phase stability of the vesicle may be decreased.

Examples 18 and 21 to 25 were made with different contents of the saturated lecithin, and it is found by comparing Examples 18 and 21 to 25 with each other that Example 21 has a phase isolated after 7 days, Examples 18 and 23 to 25 have phases that are maintained very stable even after 14 days, and Example 22 is decreased in the phase stability after 7 days. In other words, if the content of the saturated lecithin contained in the intercorneocyte lipid mimetics is less than or equal to wt %, the intercorneocyte lipid mimetics may not be stabilized, and the phase stability of the vesicle may be decreased.

Examples 18 and 26 to 28 were made with different total contents of the intercorneocyte lipid components (ceramide, phytosterol, phytosterol macadamia nut fatty acid ester, the palmitic acid, the stearic acid, the oleic acid, and the linoleic acid). It is found by comparing Examples 18 and 26 to 28 with each other that Example 28 has a phase isolated after 7 days, Examples 18 and 26 have phases that are maintained very stable even after 14 days, and Example 27 is decreased in the phase stability after 7 days. In other words, if the total content of the kintercorneocyte lipid components contained in the intercorneocyte lipid mimetics is less than or equal to 74 wt %, the intercorneocyte lipid mimetics may not be stabilized, and the phase stability of the vesicle may be decreased.

Examples 29 to 34 were made with different contents of the lysolecithin, and it is found by comparing Examples 29 to 34 with each other that Example 29 has a phase isolated after 24 hours, Examples 30 to 34 have phases that are maintained very stable even after 14 days, and Example 30 is decreased in the phase stability after 14 days. In other words, if the content of the lysolecithin contained in the vesicle is less than or equal to 0.5 wt %, the intercorneocyte lipid mimetics may not be stabilized, and the phase stability of the vesicle may be decreased.

Comparative examples 1 to 3 were made with different total contents of ceramide, phytosterol, phytosterol macadamia nut fatty acid ester, the palmitic acid, the stearic acid, the oleic acid, and the linoleic acid, and it is found that the isolation of the phases appears earlier as the total content of ceramide, phytosterol, phytosterol macadamia nut fatty acid ester, the palmitic acid, the stearic acid, the oleic acid, and the linoleic acid increases.

Comparing Comparative example 1 with Example 16, it is found that although the total content of ceramide, phytosterol, phytosterol macadamia nut fatty acid ester, the palmitic acid, the stearic acid, the oleic acid, and the linoleic acid is smaller than that of Example 16, the isolation of the phases appears earlier. Meanwhile, in Example 26 and Comparative example 3, the total content of ceramide, phytosterol, phytosterol macadamia nut fatty acid ester, the palmitic acid, the stearic acid, the oleic acid, and the linoleic acid is the same, and Example 26 has a phase that is maintained very stable even after 14 days, whereas Comparative example 3 has a phase isolated after one hour. In other words, in the vesicle containing the intercorneocyte lipid components, it is found that the vesicle formed according to the present invention is excellent in the phase stability than a single membrane vesicle.

<Test Example 2> Evaluation of Skin Irritation

In order to examine the stability of the vesicles produced in Examples 15 to 34 with respect to the skin, the skin irritation was evaluated, and the evaluation results are shown in Table 8 below.

The test was performed on 42 adult women aged between 30 to 50 years without a skin disease, and conducted on an upper arm of a subject while avoiding a portion having skin damage, excessive hair, or a significant difference in color tone. A patch including 0.1 g of each of the vesicles of Examples 15 to 34 was applied to the skin, and a patch of 0.1 g of purified water was applied to the skin as a control group. Thereafter, the skin was left for 24 hours, the patches are detached, and a skin response was examined and scored for evaluation.

TABLE 8

|  | Control group | Example 15 | Example 16 | Example 17 | Example 18 | Example 19 | Example 20 | Example 21 | Example 22 | Example 23 | Example 24 |
|---|---|---|---|---|---|---|---|---|---|---|---|
| Before patch | 0 | 0 | 0 | 0 | 0 | 0 | 0 | 0 | 0 | 0 | 0 |
| 24 hours later | 0 | 0 | 0 | 0 | 0 | 0 | 0 | 2 | 0 | 0 | 0 |

TABLE 8-continued

| | Control group | Example 25 | Example 26 | Example 27 | Example 28 | Example 29 | Example 30 | Example 31 | Example 32 | Example 33 | Example 34 |
|---|---|---|---|---|---|---|---|---|---|---|---|
| Before patch | 0 | 0 | 0 | 0 | 0 | 0 | 0 | 0 | 0 | 0 | 0 |
| 24 hours later | 0 | 1 | 0 | 0 | 0 | 0 | 0 | 0 | 0 | 0 | 1 |

0: No response,
1: Faint erythema,
2: Erythema,
3: Edema,
4: Phlyctenule

Comparing Examples 15 to 20 with each other, it is found that no skin irritation was incurred in Examples 15 to 19, whereas erythema was observed in Example 20, which indicates occurrence of the skin irritation. In other words, if the content of the surfactant contained in the intercorneocyte lipid mimetics is greater than or equal to 25 wt %, it is found that the content of the surfactant is excessive, so that the surfactant causes the skin irritation.

Comparing Examples 18 and 21 to 25 with each other, it is found that no skin irritation was incurred in Examples 18 and 21 to 24, whereas slight erythema was observed in Example 25, which indicates occurrence of the skin irritation. In other words, if the content of the saturated lecithin contained in the intercorneocyte lipid mimetics is greater than or equal to 25 wt %, it is found that the saturated lecithin causes the skin irritation.

Comparing Examples 18 and 26 to 28 with each other, no skin irritation was observed in Examples 18 and 26 to 28. It is found that no skin irritation was incurred even if the content of the intercorneocyte lipid components increases.

Comparing Examples 29 to 34 with each other, it is found that no skin irritation is incurred in Examples 29 to 33, whereas slight erythema was observed in Example 34, which indicates occurrence of the skin irritation. In other words, if the content of the lysolecithin contained in the vesicle is greater than or equal to 20 wt %, it is found that the lysolecithin causes the skin irritation.

<Test Example 3> Evaluation of Expression of Filaggrin

Figure 2:
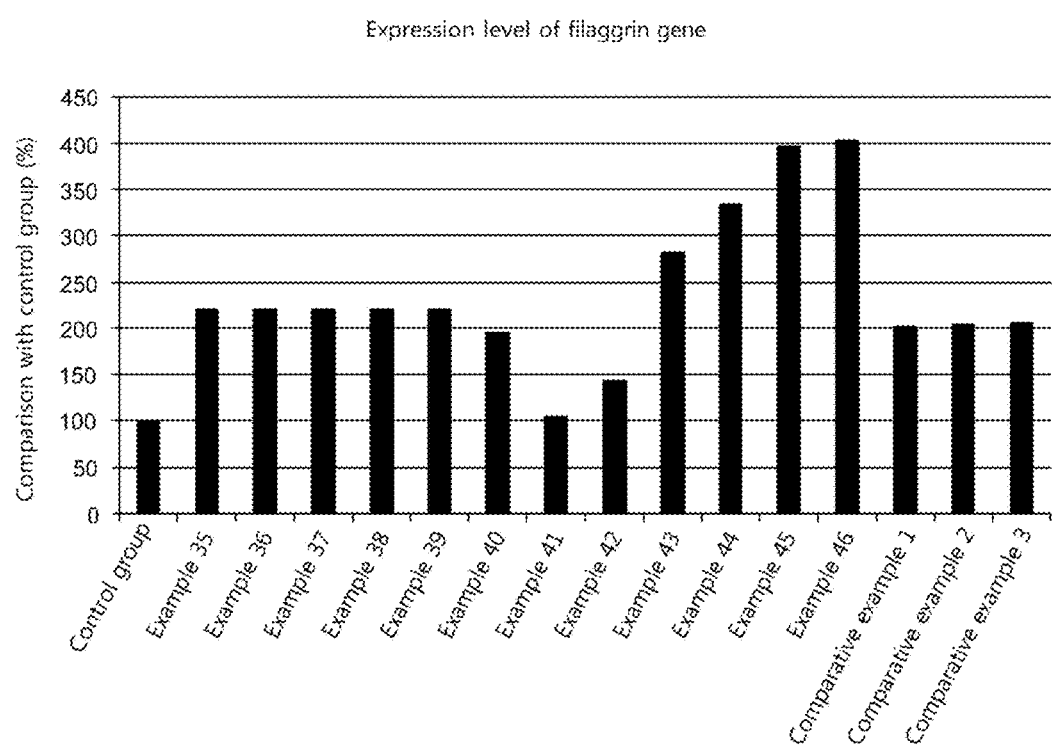
FIG. 2 is a graph showing an expression effect of filaggrin in the vesicle prepared according to one embodiment of the present invention.

In order to examine effects of the vesicle produced in Examples 35 to 46 and the single membrane vesicles of Comparative examples 1 to 3 on the expression of filaggrin, the keratinocytes were treated with the vesicles produced in Examples 35 to 46 and the single membrane vesicles of Comparative examples 1 to 3, the expression of filaggrin was examined through a reverse transcription polymerase chain reaction (RT-PCR), and the examination results are shown in FIG. 2.

1) Cultivation of Corneocytes and Treatment of Test Substances

The cell line used in the experiment was a keratinocyte distributed from American Type Culture Collection (ATCC) (Human keratinocyte HaCaT cell line). 1×105 cells were seeded on a 35 mm plate, and cultured in Dulbecco's Modified Eagle's Medium (DMEM) containing 10% of fetal bovine serum (FBS) and 1% of penicillin-streptomycin at 37° C. in 5% of $CO_2$ for one day. After 1 day of culture, the medium was removed before treating the test substance, a serum component was removed from the medium by washing with phosphate buffered saline (PBS), and the test substance was treated on a DMEM without the FBS at a concentration of 10% and cultured in a $CO_2$ incubator for 24 hours. The vesicles produced in Examples 35 to 46 and Comparative examples 1 to 3 were used as the test substances, and the control group was cultured in a medium identical to the above-mentioned medium without adding the test substance.

2) Expression Measurement of Filaggrin

A total amount of RNA was extracted from the cells cultured by the above method using Trizol (Gibco Laboratories, USA), and an RT-PCR analysis was performed according to a method provided in a one-step RNA PCR kit (AMV; Takara Bio Inc., Japan). The PCR amplification was performed using GeneAmp® PCR System 2700 (Applied Biosystems, Foster City, USA) by denaturing at 94° C. for 30 seconds, annealing at 60° C. for 30 seconds, and allowing to expand at 72° C. for 75 seconds. The PCR product was electrophoresed in 1% agarose gel stained with SYBR Safe DNA gel stain (Invitrogen, Carlsbad, USA), and a band expressed through the electrophoresis was examined. At this time, a primer for filaggrin (Macrogen, Korea, forward 5'-TCAGTTAGGATGGTGAATGTG-3', reverse 5'-TCAAAAGACAAATCCAAGCT-3') was used, and an expression level of filaggrin was compared to an internal control group of β-actin.

3) Results

As shown in FIG. 2, it is found that the expression of filaggrin in Examples 35 to 46 and Comparative examples 1 to 3 is increased as compared with the control group.

Examples 35 to 40 were made with different contents of the intercorneocyte lipid mimetics, and it is found by comparing Examples 35 to 40 with each other that expression levels of filaggrin in Examples 35 to 39 are the same, whereas an expression level of filaggrin in Example 40 is decreased. In other words, if the content of the intercorneocyte lipid mimetics contained in the vesicle is greater than or equal to 80 wt %, the content of the saccharide isomerate contained in the vesicle is relatively decreased, so that the expression of filaggrin is inhibited.

Examples 41 to 46 were made with different contents of the saccharide isomerate, and it is found by comparing Examples 41 to 46 with each other that the expression of filaggrin is increased as the content of the saccharide isomerate increases, and the expression of filaggrin in Example 41 is rarely different from the expression of filaggrin of the control group. In addition, comparing Example 46 with Example 45, the expression of filaggrin in Example 46 is increased than the expression of filaggrin in Example 45. However, it is found that a degree of the expression of filaggrin being enhanced according to increase in the content of the saccharide isomerate in Examples 45 and 46 is smaller than a degree of the expression of filaggrin being enhanced according to increase in the content of the saccharide isomerate in Examples 42 to 45.

Although the content of the saccharide isomerate is the same in Comparative examples 1 to 3 and Examples 35 to 39, it is found that the expression of filaggrin is improved in Examples 35 to 39 than in Comparative examples 1 to 3. In seems that the above result is obtained because the vesicles of Examples 35 to 39 contain the intercorneocyte lipid mimetics stabilized by saturated lecithin together with the saccharide isomerate, so that the skin moisturizing effect is complemented due to the intercorneocyte lipid mimetics.

<Test Example 4> Evaluation of Expression of Laminin-5

In order to examine effects of the vesicles produced in Examples 35 to 46 and the single membrane vesicles of Comparative examples 1 to 3 on the expression of laminin-5, culturing of the keratinocytes and treatment of the test substance were performed in the same manner as in Test example 3 described above. The vesicles produced in Examples 35 to 46 and Comparative examples 1 to 3 were used as the test substances, and the control group was cultured in a medium identical to the above-mentioned medium without adding the test substance.

1) Expression Measurement of Laminin

Laminin-5 present in a culture supernatant and a cell layer was measured by a sandwich enzyme-linked immunosorbent assay (ELISA). A monoclonal antibody (BMI65) against an α3 chain of laminin-5 was bound to a solid layer of a 96-well ELISA plate. In order to measure laminin-5 by sandwiching, another monoclonal antibody (6F12) against β3 chain of laminin was previously biotinylated (b-6F12) and used. In the present method, only the heterotrimer (α3β3γ2) capable of exhibiting a function is measured, and the heterodimer (β3γ2) is not detected. The test substance was added to each of wells where 3% gelatin.phosphate buffer solution containing b-6F12 had been previously introduced, and a final dilution rate of the test substance in each well was ¼ in case of the culture solution and ¹/₁₀ in case of the cell layer. The antigen-antibody reaction was performed at 37° C. for two hours, the plate is washed, an avidin horseradish peroxidase (HRP) solution was added, and the reaction was performed again for 30 minutes for one hour. After washing, an ABTS solution, which is a substrate of HRP, was added, and absorbance was measured at a wavelength of 405 nm using an ELISA plate reader. A calibration curve was prepared in a range of 0 ng/ml to 40 ng/ml, and a production amount of laminin-5 was expressed as a percentage of a total amount calculated by summing up an amount of laminin-5 isolated in the medium and an amount of laminin-5 remaining in the cell layer with respect to a sample where the test substance was not added (control group). The examination results are shown in FIG. 3.

2) Results

Figure 3:
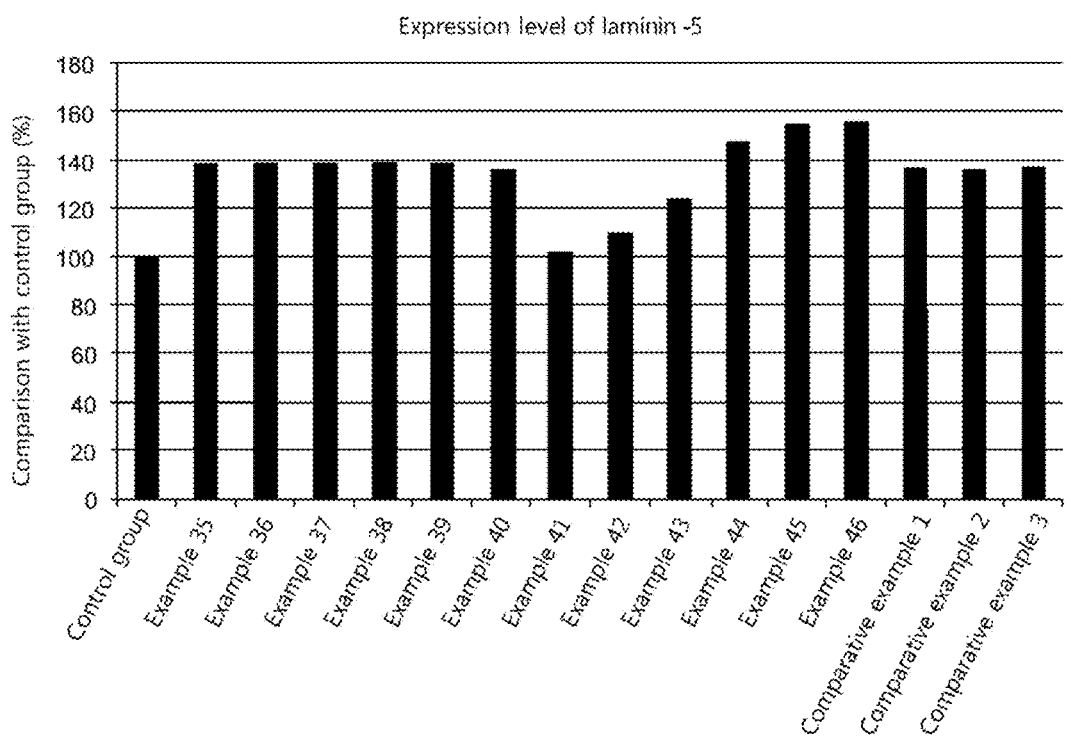
FIG. 3 is a graph showing an expression effect of laminin-5 in the vesicle prepared according to one embodiment of the present invention.

As shown in FIG. 3, it is found that the expression of laminin-5 in Examples 35 to 46 and Comparative Examples 1 to 3 is increased as compared with the control group.

Comparing Examples 35 to 40 with each other, it is found that expression levels of laminin-5 in Examples 35 to 39 are the same, whereas an expression level of laminin-5 in Example 40 is decreased. In other words, if the content of the intercorneocyte lipid mimetics contained in the vesicle is greater than or equal to 80 wt %, the content of the hydrolyzed lupine protein contained in the vesicle is relatively decreased, so that the expression of laminin-5 is inhibited.

Comparing Examples 41 to 46 with each other, it is found that the expression of laminin-5 is increased as the content of the hydrolyzed lupine protein increases, and the expression of laminin-5 in Example 41 is rarely different from the expression of laminin-5 of the control group. In addition, comparing Example 46 with Example 45, the expression of laminin-5 in Example 46 is increased than the expression of laminin-5 in Example 45. However, it is found that a degree of the expression of laminin-5 being enhanced according to increase in the content of the hydrolyzed lupine protein in Examples 45 and 46 is smaller than a degree of the expression of laminin-5 being enhanced according to increase in the content of the hydrolyzed lupine protein in Examples 42 to 45.

Although the content of the hydrolyzed lupine protein is the same in Comparative examples 1 to 3 and Examples 35 to 39, it is found that the expression of laminin-5 is improved in Examples 35 to 39 than in Comparative examples 1 to 3. In Seems that the above result is obtained because the vesicles of Examples 35 to 39 contain the intercorneocyte lipid mimetics stabilized by saturated lecithin together with the hydrolyzed lupine protein, so that the skin moisturizing effect is complemented due to the intercorneocyte lipid mimetics.

<Test Example 5> Evaluation of Increase in Expression of Type 4 Collagen

In order to examine effects of the vesicles produced in Examples 35 to 46 and the single membrane vesicles of Comparative examples 1 to 3 on the expression of type 4 collagen, culturing of the keratinocytes and treatment of the test substance were performed in the same manner as in Test example 3 described above. The vesicles produced in Examples 35 to 46 and Comparative examples 1 to 3 were used as the test substances, and the control group was cultured in a medium identical to the above-mentioned medium without adding the test substance.

1) Expression Measurement of Type 4 Collagen

A total amount of RNA was extracted from the cells cultured by the above method using Trizol (Gibco Laboratories, USA), and an RT-PCR analysis was performed according to a method provided in a one-step RNA PCR kit (AMV; Takara Bio Inc., Japan). The PCR amplification was performed using GeneAmp® PCR System 2700 (Applied Biosystems, Foster City, USA) by denaturing at 94° C. for 30 seconds, annealing at 60° C. for 30 seconds, and allowing to expand at 72° C. for 75 seconds. The PCR product was electrophoresed in 1% agarose gel stained with SYBR Safe DNA gel stain (Invitrogen, Carlsbad, USA), and a band expressed through the electrophoresis was examined. At this time, a primer for type 4 collagen (Macrogen, Korea, forward 5'-CCTGGTCTTGAAAGGTGATAAG-3', reverse 5'-CCCGCTATCCCTTGATCTC-3') was used, and an expression level of type 4 collagen was compared to an internal control group of β-actin. The examination results are shown in FIG. 4.

2) Results

Figure 4:
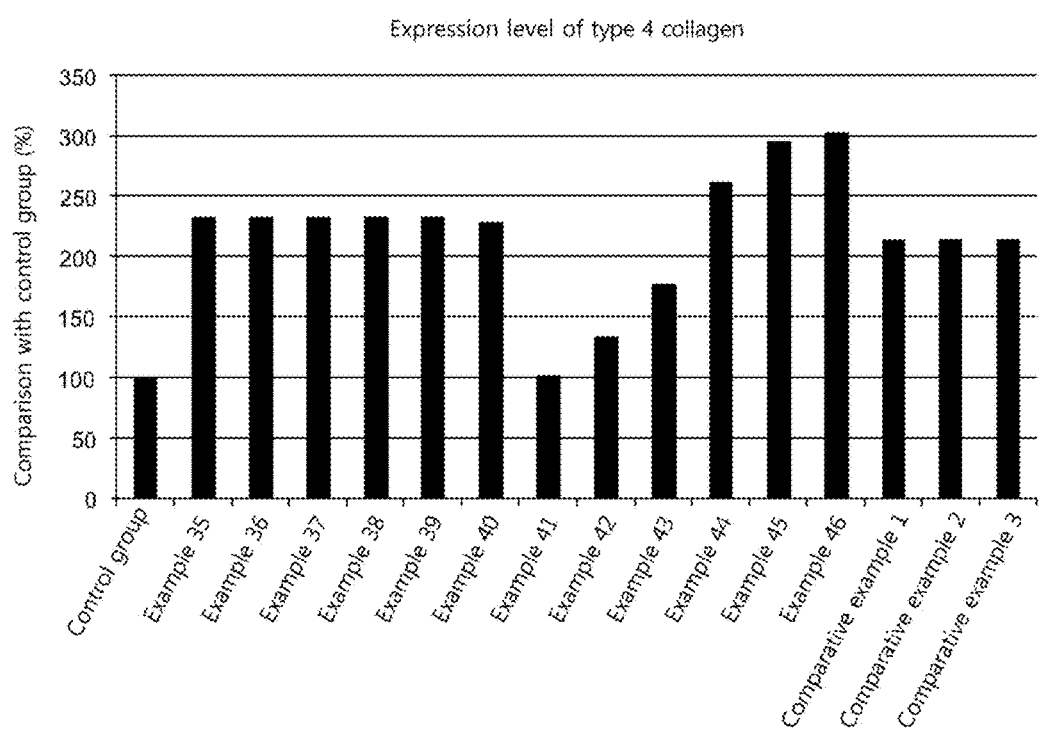
FIG. 4 is a graph showing an expression effect of type 4 collagen in the vesicle prepared according to one embodiment of the present invention.

As shown in FIG. 4, it is found that the expression of type 4 collagen in Examples 35 to 46 and Comparative examples 1 to 3 is increased as compared with the control group.

Comparing Examples 35 to 40 with each other, it is found that expression levels of type 4 collagen in Examples 35 to 39 are the same, whereas an expression level of type 4 collagen in Example 40 is decreased. In other words, if the content of the intercorneocyte lipid mimetics contained in the vesicle is greater than or equal to 80 wt %, the content of the hydrolyzed lupine protein contained in the vesicle is relatively decreased, so that the expression of type 4 collagen is inhibited.

Comparing Examples 41 to 46 with each other, it is found that the expression of type 4 collagen is increased as the content of the hydrolyzed lupine protein increases, and the expression of type 4 collagen in Example 41 is rarely different from the expression of type 4 collagen of the control group. In addition, comparing Example 46 with Example 45, the expression of type 4 collagen in Example 46 is increased than the expression of type 4 collagen in Example 45. However, it is found that a degree of the expression of type 4 collagen being enhanced according to increase in the content of the hydrolyzed lupine protein in Examples 45 and 46 is smaller than a degree of the expression of type 4 collagen being enhanced according to increase in the content of the hydrolyzed lupine protein in Examples 42 to 45.

Although the content of the hydrolyzed lupine protein is the same in Comparative examples 1 to 3 and Examples 35 to 39, it is found that the expression of type 4 collagen is improved in Examples 35 to 39 than in Comparative examples 1 to 3. In seems that the above result is obtained because the vesicles of Examples 35 to 39 contain the intercorneocyte lipid mimetics stabilized by saturated lecithin together with the hydrolyzed lupine protein, so that the skin moisturizing effect is complemented due to the intercorneocyte lipid mimetics.

<Test Example 6> Measurement and Evaluation of Transepidermal Water Loss (TEWL)

In order to examine the skin moisturizing effect of the vesicles of Examples 36 to 39 and the single membrane vesicle of Comparative example 3, the TEWL was measured by a Tewameter.

1) Measurement of TEWL

The measurement was performed on 28 adult women aged between 30 to 40 years without a skin disease, and performed on an upper arm of a subject while avoiding a portion having skin damage, excessive hair, or a significant difference in color tone. Test sites of the subjects were kept clean and dry in order to make measurement conditions the same, and the skin was stabilized at a temperature of 22±2° C., and a humidity of 50±10% for at least 30 minutes before the measurement. The TEWL of the test site was measured before use, one week after use, and two weeks after use by the Tewameter (TM300, Courage and Khazaka electronic GmbH, Germany). Measurements were taken for about 20 seconds until a value is stabilized, and an average of three values selected by excluding the maximum and minimum values from five stabilized values was obtained. Using the TEWL measured before use as a default value, improvement rates of the TEWL measured one week after use and the TEWL measured two weeks after use were calculated, and the calculation results are shown in FIG. 5.

2) Results

Figure 5:
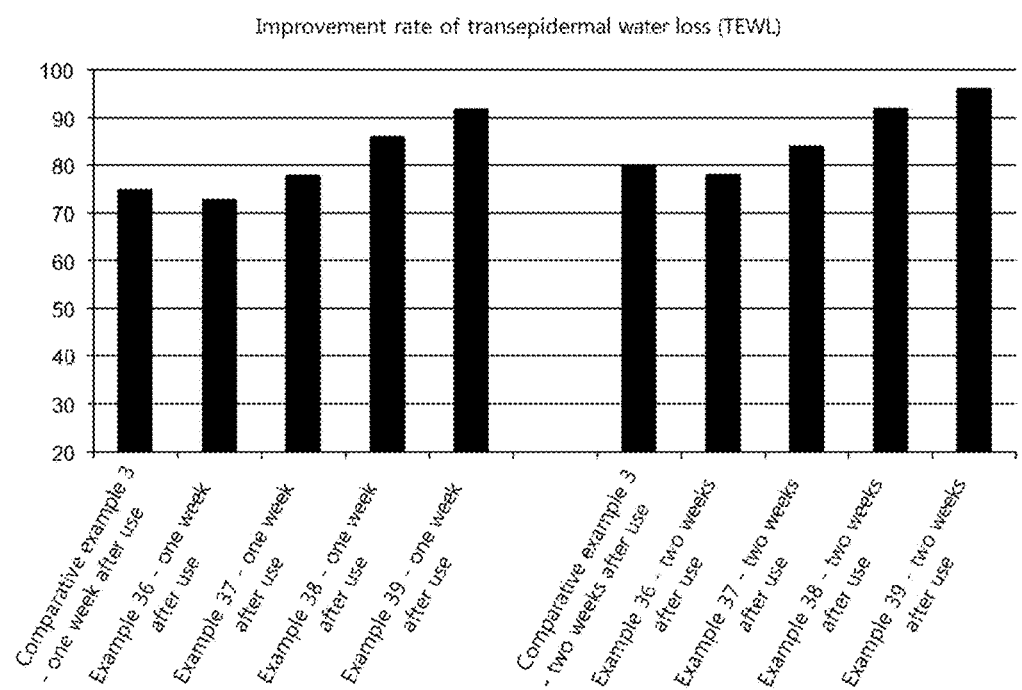
FIG. 5 is a graph showing an effect of improving TEWL in the vesicle prepared according to one embodiment of the present invention.

As shown in FIG. 5, comparing Examples 36 to 40 with each other, it is found that the improvement rate of the TEWL is increased as the content of the intercorneocyte lipid mimetics contained in the vesicle increases. In Example 38 and Comparative example 3, the content of the intercorneocyte lipid components contained in the vesicle is the same, and the improvement rate of the TEWL is higher in Example 38 than in Comparative example 3. In addition, it is found that the improvement rate of the TEWL in Comparative example 3 is lower than that in Example 37 where the content of the intercorneocyte lipid components contained in the vesicle is small. In other words, the intercorneocyte lipid components contained in the single membrane vesicle may not be stabilized, so that the intercorneocyte lipid components contained in the single membrane vesicle may not be effectively absorbed into the skin, thereby decreasing the skin moisturizing effect.

<Test Example 7> Skin Moisturizing Effect

In order to examine the skin moisturizing effect of the vesicles of Examples 36 to 40 and the single membrane vesicle of Comparative example 3, the skin moisturizing ability was evaluated by a Corneometer.

1) Measurement of Skin Moisturizing Ability

The measurement was performed on 28 adult women aged between 30 to 40 years without a skin disease, and performed on an upper arm of a subject while avoiding a portion having skin damage, excessive hair, or a significant difference in color tone. Test sites of the subjects were kept clean and dry in order to make measurement conditions the same, and the skin was stabilized at a temperature of 22±2° C., and a humidity of 50±10% for at least 30 minutes before the measurement. The measurement of the skin moisturizing ability was performed by measuring a skin conductivity using the Corneometer (CM825, Courage and Khazaka Electronic GmbH, Germany), and the average value was obtained using three values except for the maximum value and the minimum value. Using the skin conductivity measured before use as a default value, rates of increase in skin moisture is evaluated by measuring skin conductivities one hour after use, three hours after use, and 30 minutes after washing a face, and the evaluation results are shown in FIG. 6.

2) Results

Figure 6:
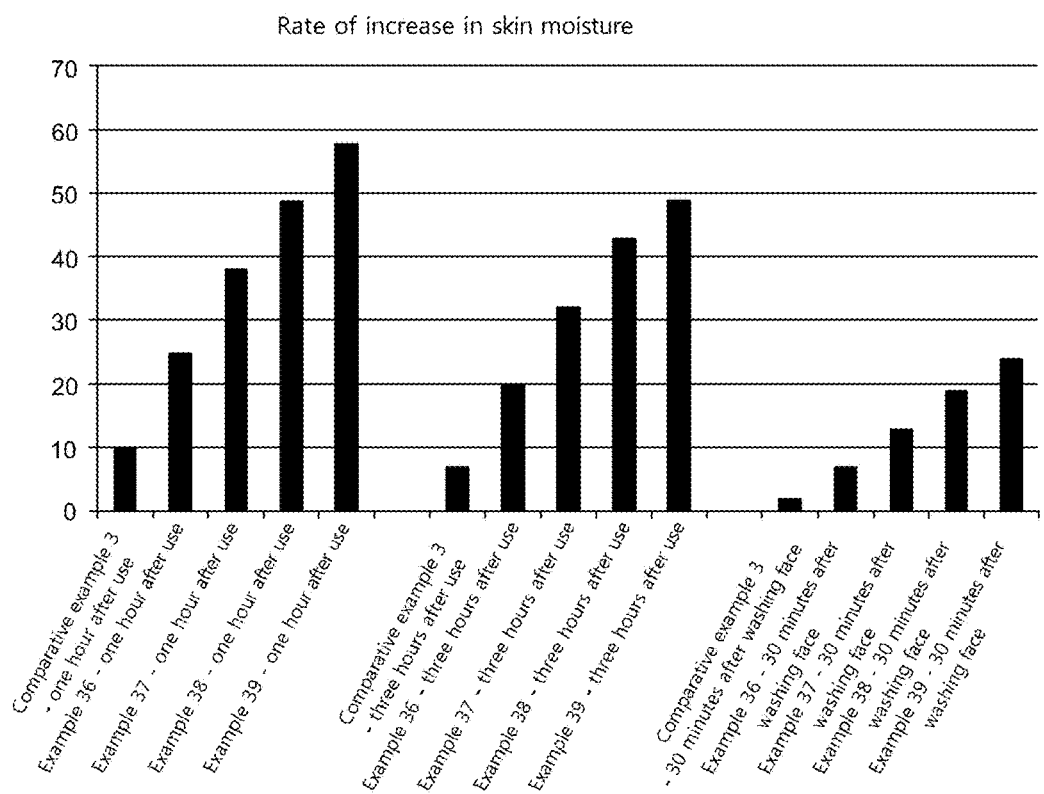
FIG. 6 is a graph showing an effect of increasing skin moisture in the vesicle prepared according to one embodiment of the present invention.

As shown in FIG. 6, comparing Examples 36 to 40 with each other, it is found that an amount of moisture remaining in the skin is increased as the content of the intercorneocyte lipid mimetics contained in the vesicle increases. Comparing Example 38 and Comparative example 3, the content of moisture presentin the skin is higher in Example 38 than in Comparative example 3. In addition, it is found that the content of moisture present in the skin in Comparative example 3 is lower than that in Example 37 where the content of the intercorneocyte lipid components contained in the vesicle is small. In other words, the intercorneocyte lipid components contained in the single membrane vesicle may not be stabilized, so that the intercorneocyte lipid components contained in the single membrane vesicle may not be effectively absorbed into the skin, thereby decreasing the skin moisturizing effect.

What is claimed is:

1. A vesicle containing a saccharide isomerate, a hydrolyzed lupine protein, and an intercorneocyte lipid mimetics as an active ingredient, the vesicle comprising:
 an oil phase part obtained by dispersing 10 wt % to 75 wt % of the intercorneocyte lipid mimetics and 1 wt % to 10 wt % of lysolecithin in 1 wt % to 20 wt % of glycerin; and
 an aqueous phase part obtained by dissolving 0.01 wt % to 7 wt % of the saccharide isomerate and 0.01 wt % to 7 wt % of the hydrolyzed lupine protein in the balance of purified water, wherein the intercorneocyte lipid mimetics includes 10 wt % to 70 wt % of an intercorneocyte lipid component, 0.1 wt % to 20 wt % of an amphoteric surfactant, 2 wt % to 20 wt % of saturated lecithin, 5 wt % to 20 wt % of glycerin, and the balance of purified water based on a total weight of the intercorneocyte lipid mimetics.

2. The vesicle of claim 1, wherein the intercorneocyte lipid component includes 5 wt % to 60 wt % of ceramide, 5 wt % to 35 wt % of a cholesterol derivative containing cholesterol or a phytosterol derivative containing phytosterol, and 5 wt % to 60 wt % of a higher fatty acid based on a total weight of the intercorneocyte lipid component.

3. The vesicle of claim 2, wherein the higher fatty acid is obtained by mixing palmitic acid:stearic acid: oleic acid: linolenic acid in a weight ratio of 1 to 5:1 to 10:1 to 6:1 to 4.

4. The vesicle of claim 1, wherein the vesicle enhances a skin barrier function and a skin moisturizing effect by increasing expression of filaggrin, laminin-5, and type-4 collagen.

5. A composition for skin external application comprising the vesicle containing the saccharide isomerate, the hydrolyzed lupine protein, and the intercorneocyte lipid mimetics as the active ingredient according to claim 1.

6. The composition of claim 5, wherein the composition comprises one type of formulation selected from the group consisting of a liquid, a suspension, an emulsion, a gel, a cream, an ointment, a spray, and a paste.

* * * * *